United States Patent [19]

Shinoda

[11] Patent Number: 5,283,057
[45] Date of Patent: Feb. 1, 1994

[54] RISEDRONATE IN ORAL COMPOSITIONS

[75] Inventor: Hisashi Shinoda, Sendai, Japan

[73] Assignee: The Proctor & Gamble Company, Cincinnati, Ohio

[21] Appl. No.: 874,269

[22] Filed: Apr. 24, 1992

[51] Int. Cl.$^5$ .......................... A61K 7/16; A61K 7/22
[52] U.S. Cl. ........................................ 424/54; 514/79; 514/85; 514/89; 514/102; 514/900; 514/902; 433/215
[58] Field of Search ................... 424/54; 514/79, 85, 514/89, 102, 900, 902

[56] References Cited

U.S. PATENT DOCUMENTS

| | | | |
|---|---|---|---|
| 4,208,401 | 6/1980 | Bauman | 424/54 |
| 4,871,720 | 10/1989 | Jaeggi | 514/79 |
| 5,036,058 | 7/1991 | Jaeggi | 514/86 |

FOREIGN PATENT DOCUMENTS

| | | |
|---|---|---|
| 186405 | 7/1986 | European Pat. Off. . |
| 274158 | 7/1988 | European Pat. Off. . |
| 291747 | 11/1988 | European Pat. Off. . |
| 350002 | 1/1990 | European Pat. Off. . |
| 407344 | 1/1991 | European Pat. Off. . |
| 416689 | 3/1991 | European Pat. Off. . |
| 480811 | 4/1992 | European Pat. Off. . |
| 4011777 | 10/1990 | Fed. Rep. of Germany ... C07F 9/38 |
| 8800829 | 2/1988 | PCT Int'l Appl. . |
| 9200721 | 1/1992 | PCT Int'l Appl. . |

OTHER PUBLICATIONS

Ebetino et al CA 113:212124V (1990).
Sietsema et al CA 112:191396x (1990).
Ebetino et al CA 109:222488y (1988).
Procter & Gamble CA 106:90180t (1987).
Benedict et al CA 105:232453q (1986).
Francis et al CA 112:191900Q (1989).
Wronski et al CA 111:127227v (1989).
Hughes et al CA 111:108823v (1989).

*Primary Examiner*—Shep K. Rose
*Attorney, Agent, or Firm*—D. C. Mohl; D. K. Dabbiere; J. C. Rasser

[57] ABSTRACT

The present invention relates to compositions and methods which are effective against alveolar bone resorption and enhance the ability of a tooth moved in orthodontic therapy to remain in its new position or to stay in its original position when adjacent teeth are moved.

11 Claims, No Drawings

RISEDRONATE IN ORAL COMPOSITIONS

TECHNICAL FIELD

The present invention relates to compositions and methods which are effective against alveolar bone resorption and stabilization of teeth which have been moved in orthodontic therapy.

BACKGROUND OF THE INVENTION

Problems are faced in orthodontic therapy in that when teeth are moved they have the tendency to move back towards their original position or teeth that are not intended to be moved do move. To resist this, the underlying bone structure must not be allowed to be weakened or lost. Bone loss is extremely dangerous and causes the support for the teeth to be lost and subsequently the teeth themselves. In addition, alveolar bone resorption is a problem faced in subjects suffering from periodontal disease.

Several different therapy processes have been used to treat alveolar bone resorption. However there is still a need to find improved therapies. The present inventor has found that certain geminal diphosphonic acid compounds, including their salts and esters, in which the diphosphonic acid-containing carbon is linked to a 6 member aromatic ring containing one or more nitrogen atoms are effective against alveolar bone loss and unwanted tooth movement.

It is an object of the present invention to provide compositions which are effective against alveolar bone loss and unwanted tooth movement.

It is a further object of the present invention to provide methods employing diphosphonate salts to treat alveolar bone resorption and unwanted tooth movement.

These and other objects will become more evident from the detailed description which follows.

All percentages and ratios used herein are by weight of the total composition unless otherwise specified and all measurements are made at 25° C.

SUMMARY OF THE INVENTION

The present invention embraces an oral composition comprising:

a) from about 0.002% to about 10.000% of a geminal diphosphonic acid compound, or a pharmaceutically-acceptable salt or ester thereof, having the structure:

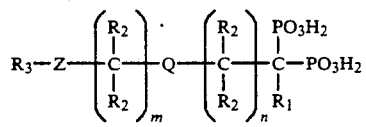

wherein Z is a ring selected from the group consisting of pyridine, pyridazine, pyrimidine and pyrazine; Q is oxygen, —NR$_4$—, or a single bond; m+n is an integer from 0 to about 5; R$_1$ is hydrogen, substituted or unsubstituted amino, amido, hydroxy, alkoxy, halogen, carboxylate, substituted or unsubstituted, saturated or unsaturated alkyl having from 1 to about 6 carbon atoms, substituted or unsubstituted aryl, or substituted or unsubstituted benzyl, except that when n=0 and Q is oxygen or nitrogen, then R$_1$ is hydrogen, substituted or unsubstituted, saturated or unsaturated alkyl having from 1 to about 6 carbon atoms, substituted or unsubstituted aryl, or substituted or unsubstituted benzyl; R$_2$ is hydrogen, or substituted or unsubstituted, saturated or unsaturated alkyl having from 1 to about 4 carbon atoms; R$_3$ is one or more substituents selected from the group consisting of hydrogen, substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof; R$_4$ is hydrogen, substituted or unsubstituted, saturated or unsaturated alkyl having from 1 to about 4 carbon atoms, or acyl.

b) a carrier suitable for placing component (a) into the oral cavity.

The present invention also encompasses a method of combatting alveolar bone resorption and the tendency for teeth moved during orthodontic therapy to move back to their original position or the tendency for teeth to move when adjacent teeth are moved.

By "carrier suitable for placing the diphosphonate into the oral cavity" as used herein means a carrier which in the ordinary course of usage is suitable for use in the mouth.

By "safe and/or effective amount" as used herein means sufficient amount of material to provide the desired benefit while being safe.

DETAILED DESCRIPTION OF THE INVENTION

The essential as well as optional components of the present invention are described in the following paragraphs.

Diphosphonic Acid

This invention relates to oral compositions, comprising a safe and effective amount of geminal diphosphonic acid compounds, or their pharmaceutically-acceptable salts and esters, in which the diphosphonic acid-containing carbon is linked to a 6 membered aromatic ring containing one or more nitrogen atoms. Preferred rings are pyridine, pyridazine, pyrimidine, and pyrazine. Most preferred are pyrimidine, and especially pyridine. The rings may be unsubstituted alkyl (saturated or unsaturated) having from 1 to about 6 carbon atoms, substituted and unsubstituted aryl (e.g., phenyl and naphthyl), substituted and unsubstituted benzyl, hydroxy, halogen, carbonyl (e.g., —CHO and —COCH$_3$), alkoxy (e.g., methoxy and ethoxy), nitro, amido (e.g., —NHCOCH$_3$), amino, substituted amino (e.g., dimethylamino, methylamino, and diethylamino), carboxylate (e.g., —OCOCH$_3$), and combinations thereof. The rings may be fused with other rings, e.g., benzene fused with pyridine (e.g., quinoline), and cyclohexane fused with pyridine (e.g., 5,6,7,8-tetrahydroquinoline). Additional substituents could be substituted or unsubstituted sulfide, sulfoxide, sulfate, or sulfone.

The linkage from the diphosphonic acid-containing carbon to the ring may be direct through a single bond, or by a chain of length of from 1 to about 5 atoms. The chain may be all carbon atoms, a nitrogen atom or nitrogen-containing chain, an oxygen atom or oxygen-containing chain, or a selenium atom or selenium-containing chain. The carbon and nitrogen atoms in the chains may, independently, be unsubstituted or substituted with one (or one or two in the case of carbon atoms) substituted or unsubstituted alkyl (saturated or unsaturated) having from 1 to about 4 carbon atoms (methyl and ethyl being preferred). The nitrogen atoms in the chains may also be substituted with an acyl group (e.g., —COCH$_3$). Unsubstituted carbon and nitrogen atoms in the chain are preferred. Also preferred are chains one atom in length, i.e., —CH$_2$—, —NH—, and —O—.

The carbon atom which has the phosphonate groups attached to it may be unsubstituted (i.e., a hydrogen atom), or substituted with amino, substituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl. For the compounds in which the phosphonate-containing carbon is linked to the ring via an oxygen, selenium, or nitrogen-containing chain, and that oxygen, selenium, or nitrogen atom is bonded directly to the phosphonate containing carbon, then the substituent on the phosphonate-containing carbon may be substituted or unsubstituted alkyl (saturated or unsaturated) having from 1 to about 6 carbon atoms, substituted or unsubstituted aryl, or substituted or unsubstituted benzyl.

Thus, diphosphonic acid compounds to be included in the pharmaceutical compositions of the present invention have the structure:

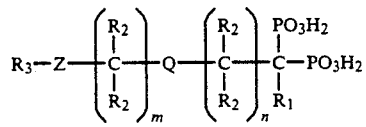

wherein Q is oxygen, —NR$_4$—, selenium, or a single bond, preferred being oxygen, —NR$_4$—, or a single bond; m+n is an integer from 0 to about 5, with m+n=0 or 1 preferred for Q being oxygen, selenium, or —NR$_4$—, and m+n=1 or 2 preferred otherwise; Z is a ring selected from the group consisting of pyridine, pyridazine, pyrimidine, and pyrazine, with preferred being pyrimidine, and especially pyridine; R$_1$ is hydrogen, substituted or unsubstituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl, except that when n=0 and Q is oxygen, selenium, or —NR$_4$— then R$_1$ is hydrogen, substituted or unsubstituted alkyl (saturated or unsaturated) having from 1 to about 6 carbon atoms, substituted or unsubstituted aryl, or substituted or unsubstituted benzyl, with R$_1$ being hydrogen, chloro, amino, methyl, or hydroxy preferred; each R$_2$ is, independently, hydrogen, or substituted or unsubstituted alkyl (saturated or unsaturated) having from 1 to about 4 carbon atoms, with R$_2$ being hydrogen preferred; R$_3$ is one or more substituents selected from the group consisting of hydrogen, substituted or unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof, with preferred being hydrogen, methyl, amino, chloro, methoxy, nitro, hydroxy and combinations thereof; R$_4$ is hydrogen, substituted or unsubstituted alkyl (saturated or unsaturated) having from 1 to about 4 carbon atoms, acyl (i.e., the amide of the nitrogen), with preferred being hydrogen, methyl, or ethyl; and pharmaceutically-acceptable salts and esters of these compounds. Finally, for any of the R$_1$, R$_2$, R$_3$, or R$_4$ substituents which are themselves substituted, the substitution on these substituents may be any one air more of the above substituents, preferred being methyl, ethyl, amino, chloro, nitro, methoxy, hydroxy, acetamido, and acetate.

More specifically, the diphosphonic acid compounds, and their pharmaceutically-acceptable salts and esters, to be included in the pharmaceutical compositions of the present invention are of the structure:

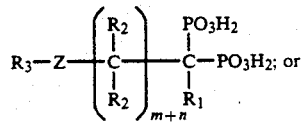

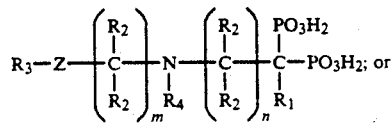

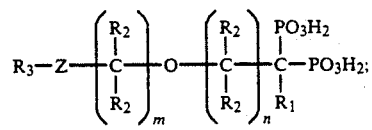

wherein m+n, Z, R$_1$, R$_2$, R$_3$, and R$_4$ are as described above.

Generally preferred diphosphonic acid compounds, and their pharmaceutically acceptable salts and esters, to be included in the pharmaceutical compositions of the present invention are of the structure:

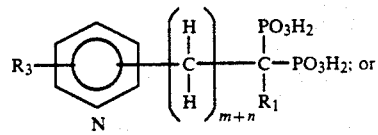

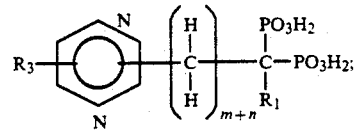

wherein for both structures above m+n=1 or 2; R$_1$ is hydrogen, chloro, amino, or hydroxy; R$_3$ is one or more substituents selected from the group consisting of hydrogen, methyl, amino, chloro, nitro, methoxy, hydroxy, and combinations thereof; or

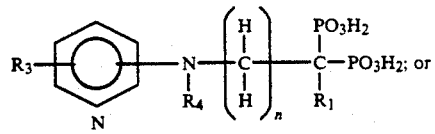

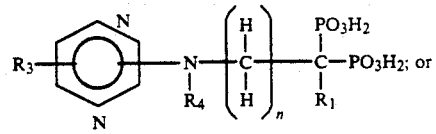

-continued

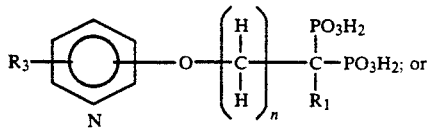

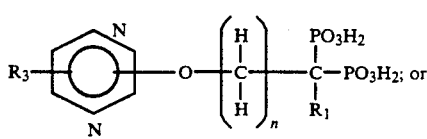

wherein for the four preceding structures n=0 or 1; $R_1$ is hydrogen, chloro, amino, or hydroxy when n=1, and $R_1$ is hydrogen when n=0; $R_3$ is one or more substituents selected from the group consisting of hydrogen, methyl, amino, chloro, methoxy, nitro, hydroxy, and combinations thereof; and $R_4$ is hydrogen, methyl, or ethyl.

Specific examples of compounds which may be utilized in compositions of the present invention include:
N-(2-pyridyl)-aminomethane diphosphonic acid;
N-(2-(5-amino)-pyridyl)-aminomethane diphosphonic acid;
N-(2-(5-chloro)-pyridyl)-aminomethane diphosphonic acid;
N-(2-(5-nitro)-pyridyl)-aminomethane diphosphonic acid;
N-(2-(3,5-dichloro)-pyridyl)-aminomethane diphosphonic acid;
N-(4-pyridyl)-N-ethyl-aminomethane diphosphonic acid;
N-(2-(3-picolyl))-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-(4,6-lutidine))-aminomethane diphosphonic acid;
N-(2-pyrimidyl)-aminomethane diphosphonic acid;
N-(4-(2,6-dimethyl)-pyrimidyl)-aminomethane diphosphonic acid;
N-(2-(4,6-dihydroxy)-pyrimidyl)-aminomethane diphosphonic acid;
N-(2-(5-methoxy)-pyridyl)-aminomethane diphosphonic acid;
N-(2-pyridyl)-2-aminoethane-1,1-diphosphonic acid;
N-(2-(3-picolyl))-2-aminoethane-1,1-diphosphonic acid;
N-(2-(4-picolyl))-2-amino-1-hydroxy-ethane-1,1-diphosphonic acid; (2-pyridyl)-methane diphosphonic acid; (3-pyridyl)-aminomethane diphosphonic acid; (2-pyridyl)-chloromethane diphosphonic acid; (4-pyridyl)-hydroxymethane diphosphonic acid; 2-(2-pyridyl)-ethane-1,1-diphosphonic acid; 2-(3-pyridyl)-ethane-1,1-diphosphonic acid; 2-(4-pyridyl)-ethane-1,1-diphosphonic acid; 2-(2-pyridyl)-1-amino-ethane-1,1-diphosphonic acid; 2-(2-pyrimidyl)-1-hydroxy-ethane-1,1-diphosphonic acid; 2-(2-(3-picolyl))-1-chloro-ethane-1,1-diphosphonic acid; 2-(2-(4-methoxy)-pyridyl)-ethane-1,1-diphosphonic acid; 1-(2-pyridyl)-propane-2,2-diphosphonic acid; 2-(2-pyridyl)-1-chloro-ethane-1,1-diphosphonic acid; 2-(2-pyridyl)-1-hydroxy-ethane-1,1-diphosphonic acid; 2-(3-pyridyl)-1-hydroxy-ethane-1,1-diphosphonic acid; 2-(4-pyridyl)-1-hydroxy-ethane-1,1-diphosphonic acid; 3-(3-pyridyl)-1-hydroxy-propane-1,1-diphosphonic acid; O-(2-pyridyl)-2-oxa-ethane-1,1-diphosphonic acid;
O-(2-pyridyl)-oxamethane diphosphonic acid;
O-(2-pyrimidyl)-oxamethane diphosphonic acid;
O-(2-(4-amino)-py?idyl)-oxamethane diphosphonic acid;
O-(2-pyrimidyl)-2-oxa-ethane-1,1-diphosphonic acid;
O-(2-(3-picolyl))-2-oxa-ethane-1,1-diphosphonic acid;
O-(2-(3-picolyl))-oxamethane-diphosphonic acid;
O-(2-pyridyl)-1-hydroxy-2-oxa-ethane-1,1-diphosphonic acid;
O-(4-pyridyl)-1-amino-2-oxa-ethane-1,1-diphosphonic acid; and
pharmaceutically-acceptable salts and esters thereof.

Preferred compounds are
N-(2-(5-amino)-pyridyl)-aminomethane diphosphonic acid;
N-(2-(5-chloro)-pyridyl)-aminomethane diphosphonic acid;
N-(2-(3-picolyl))-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-pyrimidyl)-aminomethane diphosphonic acid;
N-(2-pyridyl)-2-aminomethane-1,1-diphosphonic acid;
2-(2-pyridyl)-ethane-1,1-diphosphonic acid;
2-(3-pyridyl)-ethane-1,1-diphosphonic acid;
2-(4-pyridyl)-ethane-1,1-diphosphonic acid;
2-(2-pyridyl)-1-hydroxy-ethane-1,1-diphosphonic acid;
2-(3-pyridyl)-1-hydroxy-ethane-1,1-diphosphonic acid;
2-(4-pyridyl)-1-hydroxy-ethane-1,1-diphosphonic acid;
O-(2-(3-picolyl))-oxamethane-diphosphonic acid; and
pharmaceutically-acceptable salts and esters thereof.

The diphosphonate compounds to be included in the pharmaceutical compositions of the present invention can be made using the synthetic methods disclosed in Japanese Patent 80-98,193 (Jul. 25, 1980, to Nissan Kygaku Kagyo K.K.). Japanese Patent 80-98,105 (Jul. 25, 1980, to Nissan Chemical Industries), West German Patent 2,831,578 (Feb. 1, 1979, to Fumio), and W. Ploger et al., Z. Anorg. Allg. Chem., 389, 119 (1972), the disclosures of which are incorporated herein by reference. The aminoethane diphosphonic acid compounds, however, are best prepared as follows:

The Risedronate Active Ingredient

The term "risedronate", as used herein, denotes the diphosphonate compound 3-pyridyl-1-hydroxyethylidene-1,1-bisphosphonic acid and has the following structure:

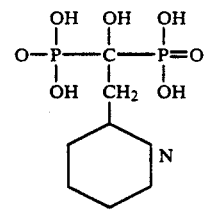

The compound risedronate is further described in the following publications, all hereby incorporated by reference herein: EPO Patent Application 0,186,405 of Benedict et al., assigned to The Procter & Gamble Co., published Jul. 2, 1986; and "An International Conference, Bisphosphonates: Current Status and Future Prospects, The Royal College of Physicians, London, England, May 21-22, 1990, organized by IBC Technical Services.

The term "risedronate active ingredient" includes risedronate, risedronate salts, and risedronate esters, or any mixture thereof. Any Pharmaceutically-acceptable, non-toxic salt or ester of risedronate may be used as the risedronate active ingredient in the novel oral dosage forms of the present invention. The salts of risedronate may be acid addition salts, in particular the hydrochloride, but any pharmaceutically-acceptable, non-toxic organic or inorganic acid salt may be used. In addition, salts formed with the carboxylic acid group may be used. In addition, salts formed with the carboxylic acid group may be used, including, but not limited to, alkali metal salts (K, Na) and alkaline earth metal salts (Ca, Mg), the Ca- and Na- salts being preferred.

Particularly, other esters of risedronate which are suitable for use as the active ingredient in the invention disclosed herein are straight chain or branched chain $C_1$-$C_{18}$ alkyl esters, including, but not limited to, methyl, ethyl, propyl, isopropyl, butyl, isobutyl, amyl, hexyl, heptyl, octyl, nonyl, decyl, lauryl, myristyl, cetyl, and stearyl; straight chain or branched $C_2$-$C_{18}$ alkenyl esters, including, but not limited to, vinyl, alkyl, undecenyl, and liholenyl; $C_3$-$C_8$ cycloalkyl esters, including, but not limited to, cyclopropyl, cyclobutyl, cyclopentyl, cyclohexyl, cycloheptyl, and cyclooctyl; aryl esters, including, but not limited to, phenyl, toluyl, xylyl, and naphthyl; alicyclic esters, including, but not limited to, menthyl; and aralkyl esters, including, but not limited to, benzyl, and phenethyl.

Generally speaking, the proper selection of the risedronate active ingredient depends on the selected type of formulation. The physical and chemical characteristics of the active ingredient must be taken into account when selecting suitable pharmaceutically-acceptable excipients for use in the novel dosage forms containing the risedronate active ingredient.

Synthesis of N-(2-(3-picolyl))aminoethane DP

The above-named compound is prepared via a typical Michael reaction between tetraethyl vinyldiphosphonate and 2-amino-3-picoline. (See H. O. House, *Modern Synthetic Reaction* 2nd Ed. W. A. Benjamin Inc. p. 595-623, the disclosure of which is incorporated herein by reference.)

To a solution of 1.62 g (15 mmol) of 2-amino-3-picoline in tetrahydrofuran at 5*C was added 4.50 g (15 mol) tetraethyl vinyldiphosphonate. The reaction mixture was stirred at room temperature for 16 hours. Evaporation of the solvent and chromatography (acetone/hexane, 4/1) of the product on silica gel gave pure tetraethyl N-(2-(3-picolyl))-2-aminoethane diphosphonate. P-31 NMR of the pure tetraethyl ester in CDCl$_3$ shows a resonance at 22.1 ppm. The ester was hydrolyzed in refluxing 6N HCl overnight. The product showed a P-31 NMR signal in D$_2$O at pH =12 of 19.0 ppm.

N-(2-pyridyl)-2-aminoethane DP and N-(2-(5-picolyl))-2-aminoethane DP were prepared in an identical manner. Compounds having the general formula

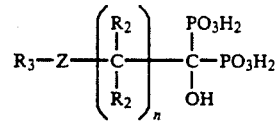

(wherein n is an integer of from 1 to about 5, preferably n=1; and Z, $R_2$ and $R_3$ are as described hereinbefore, with preferred Z being pyrimidine and especially pyridine, preferred $R_2$ being hydrogen, and preferred $R_3$ being one or more substituents selected from the group consisting of hydrogen, methyl, amino, chloro, nitro, methoxy, hydroxy, and combinations thereof) are best prepared as follows:

Synthesis of 2-(2-pyridyl)-1-hydroxy-ethane-1.1-diphosphonic acid

A 3-neck round-bottom flask fitted with a reflux condenser and a magnetic stir bar is charged with 6.94 grams (0.04 mole) 2-pyridine acetic acid, 9.84 grams (0.14 mole) phosphorus acid, and 150 ml of chlorobenzene. This reaction mixture is heated on a boiling water bath, and 16.5 grams (0.12 mole) phosphorus trichloride is added dropwise with stirring. This reaction mixture is heated for 2½ hours during which time a viscous yellow oil forms. The reaction mixture is then cooled in an ice bath and the chlorobenzene solution is decanted off from the solidified product. The reaction flask containing this solidified product is charged with 150 ml of water and heated in a boiling water bath for several hours. The hot solution is then filtered through Celite 545 ®. 300 ml of methanol is added to the warm filtrate solution, and a precipitate develops. After cooling in ice for 1 hour, the precipitate is filtered off and then washed with methanol/water (1/1 volume/volume), methanol, and ether, and air dried. The product may be recrystallized from hot water. Yield is approximately 5.9 grams (52%). The sample is characterized by P-31 and C-13 NMR.

Carrier Materials

The carrier component of the present compositions is generally an aqueous -composition. The composition can contain other components such as sodium chloride particularly in the case of an injectable solution. Other compositions topically applied include mouthwashes, toothpastes, topical gels, prophylaxis pastes and the like.

Toothpastes contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasive are described in U.S. Pat. No. 4,340,583, Jul. 29, 1982, incorporated herein by reference.

The abrasive in the toothpaste compositions described herein is present at a level of from about 6% to about 70%, preferably from about 15% to about 30%.

Flavoring agents can also be added to the dentifrice and other compositions of the present invention. Suitable flavoring agents include oil of wintergreen, oil of peppermint, oil of spearmint, oil of sassafras, and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth and polysaccharide gums such as xanthan gum can al so be used. Colloidal magnesium aluminum silicate or finely divided silica can be used as part of the thickening agent to further improve texture. Thickening agents in an amount from 0.1% to 5.0% by weight of the total composition, preferably from about 0.5% to about 4.0%, may be used.

It is also desirable to include a humectant in a toothpaste to keep it from hardening. Suitable humectants include glycerin, sorbitol, and other edible polyhydric alcohols at a level of from about 10% to about 70%.

Still another optional component for use in the compositions of the present invention is an anticalculus agent used in addition to the diphosphonate material. These agents include any which are effective against calculus such as pyrophosphate salts as disclosed in U.S. Pat. No. 4,515.772, May 7, 1985 incorporated herein by reference. The preferred agents are mono, di, tri and tetra alkali metal and aninonium pyrophosphate. Such agents are used in amounts sufficient to reduce calculus. These amounts are preferably in an amount to provide at least about 1% $P_2O_7$ ion species, more preferably at least about 1.3%, most preferably at least about 1.5%. (When used the product is diluted with water (saliva) in a ratio of 1 part of composition to 3 parts water.)

Surfactants are also useful in the compositions of this invention include many different materials. Suitable surfactants include any which are reasonably stable and function over a wide pH range. Included are non-soap anionic, nonionic, cationic, zwitterionic and amphoteric organic synthetic surfactants. Many of these are disclosed Gieseke et al. in U.S. Pat. No. 4,051,234, Sep. 27, 1988 incorporated herein in total by reference.

Preferred surfactants include alkyl sulfates, particularly Na or $NH_4$ alkyl $C_{12}$-$C_{14}$ sulfate. Any surfactant used is at a level of from about 0.2% to about 7.0%, preferably from about 0.6% to about 7%.

Polyethylene glycols are also useful in this invention can be any of a wide range of molecular weights such as from about 100 to about 1,000, preferably from about 300 to about 600. The glycol is present in an amount of from about 1% to about 10%, preferably from about 3% to about 6%. Other solvent components such as propylene glycol, dipropylene glycol, olive oil as well as others disclosed in U.S. Pat. No. 4,894,220, Jan. 16, 1990 to Nabi et al., incorporated herein by reference may be used. Other components found useful herein include polymeric components such as those described in U.S. Pat. Nos. 4,138,477 and 4,183,914, both incorporated herein by reference as well as nonionic antibacterial compounds of the type disclosed in the U.S. Pat. No. 4,894,220 mentioned above.

The following example further describes and demonstrates preferred embodiments within the scope of the present invention. The example is given solely for the purpose of illustration and is not to be construed as a limitation of this invention. Many variations are possible without departing from the invention's spirit and scope.

The present invention also involves methods of treating alveolar bone loss through the application of the compositions herein to the appropriate surfaces in the mouth.

EXAMPLE 1

The following are compositions representative of the present invention:

Aqueous solutions of risedronate are either injected or applied topically to an upper first molar in rats which has had said molar extended toward the uncial side by means of a spring for three weeks. The upper first molar or the opposite is similarly displaced and treated, not with the diphosphonate, but with 0.9% sodium chloride. The concentration of the diphosphonate in the test solutions are 125,250 and 500 micromolar and 50 ml of solution are used.

The test solutions when injected helped to prevent the displaced tooth from returning to its original position relative to the saline solution. The topical applications also have such utility particularly at the higher concentrations.

EXAMPLE 2

Given below is a composition representative of the present invention.

Sodium [2-(3-pyridyl)-1-1hydroxyethylidene]—500 μM
1, 1 bisphosphonic acid
Water—q.s. 100.00%

What is claimed is:

1. In the art of periodontal therapy or orthodontic surgery wherein a tooth is subject to avelor bone resorption or displaced or moved to a new position, or is intended to stay in its original position when an adjacent tooth is moved, or displaced the improvement effective against alevolar bone resorption, comprising the step of contacting said teeth topically, in an amount effective to prevent avelor bone resorption or prevent the displaced teeth from returning to their original position, and to stay adjacent teeth from moving from their original position during orthodontic surgery, in an oral composition comprising:

(a) from about 0.002% to about 10,000% of a geminal diphosphoric acid compound, or a pharmaceutically-acceptable salt or ester thereof, having the structure:

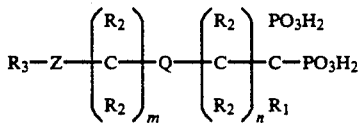

wherein Z is a ring selected from the group consisting of pyridine and pyrazine; Q is oxygen, $-NR_4-$, or a single bond; $m+n$ is an integer from 0 to about 5; $R_1$ is hydrogen, substituted of unsubstituted amino, amido, hydroxy, alkoxy, halogen, carboxylate, substituted or unsubstituted, saturated or unsaturated alkyl having from 1 to about 6 carbon atoms, substituted or unsubstituted aryl, or substituted benzyl, except that when $n=0$ and Q is oxygen or nitrogen, then $R_1$ is hydrogen, substituted or unsubstituted, saturated or unsaturated alkyl having from 1 to about 6 carbon atoms, substituted or unsubstituted aryl, or substituted of unsubstituted benzyl, $R_2$ is hydrogen, or substituted or unsubstituted, saturated or unsaturated alkyl having from 1 to about 4 carbon atoms, $R_3$ is one or more substuents selected from the group consisting of hydrogen, substituted or unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof; $R_4$ is hydrogen, substituted or unsubstituted, saturated or unsaturated alkyl having from 1 to about 4 carbon atoms, or acyl.

2. An orthodontic or peridontal method according to claim 1 wherein component (a) is characterized as from about 0.002% to about 10.000% of a geminal diphosphonic acid compound, or a pharmaceutically-acceptable salt or ester thereof, having the structure:

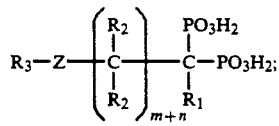

wherein Z is a ring selected from the group consisting of pyridine, pyridazine, pyrimidine and pyrazine; $m+n$ is an integer from 0 to about 5; R, is hydrogen, substituted or unsubstituted amino, amido, hydroxy, alkoxy, halogen, carboxylate, substituted or unsubstituted, saturated or unsaturated alkyl having from I to about 6 carbon atoms, substituted or unsubstituted aryl, or substituted or unsubstituted benzyl; $R_2$ is hydrogen, or substituted or unsubstituted, saturated or unsaturated alkyl having from 1 to about 4 carbon atoms; $R_3$ is one or more substituents selected from the group consisting of hydrogen, substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof.

3. An orthodontic or peridontal method according to claim 1, wherein component (a) is characterized as from about 0.002% to about 10.000% of a geminal diphosphonic acid compound, or a pharmaceutically-acceptable salt or ester thereof, having the structure:

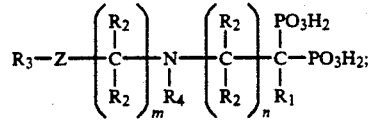

wherein Z is a ring selected from the group consisting of pyridine, pyridazine, pyrimidine and pyrazine; $m+n$ is an integer from 0 to about 5; $R_1$ is hydrogen, substituted or unsubstituted amino, amido, hydroxy, alkoxy, halogen, carboxylate, substituted or unsubstituted, saturated or unsaturated alkyl having from 1 to about 6 carbon atoms, substituted or unsubstituted aryl, or substituted or unsubstituted benzyl; $R_2$ is hydrogen, or substituted or unsubstituted, saturated or unsaturated alkyl having from 1 to about 4 carbon atoms; R3 is one or more substituents selected from the group consisting of hydrogen, substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof; $R_4$ is hydrogen, substituted or unsubstituted, saturated or unsaturated alkyl having from 1 to about 4 carbon atoms, or acyl.

4. An orthodontic or peridontal method according to claim 1 wherein component (a) is characterized as from about 0.002% to about 10.000% of a geminal diphosphonic acid compound, or a pharmaceutically-acceptable salt or ester thereof, having the structure:

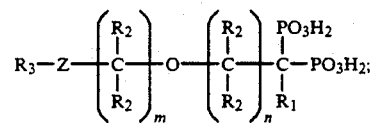

wherein Z is a ring selected from the group consisting of pyridine, pyridazine, pyrimidine and pyrazine; $m+n$ is an integer from 0 to about 5; R, is hydrogen, substituted or unsubstituted amino, amido, hydroxy, alkoxy, halogen, carboxylate, substituted or unsubstituted, saturated or unsaturated alkyl having from 1 to about 6 carbon atoms, substituted or unsubstituted aryl, or substituted or unsubstituted benzyl, except that when $n=0$, then $R_2$ is hydrogen, or substituted or unsubstituted, saturated or unsaturated alkyl having from 1 to about 6 carbon atoms, substituted or unsubstituted aryl, or substituted or unsubstituted benzyl; $R_2$ is hydrogen, or substituted or unsubstituted, saturated or unsaturated alkyl having from 1 to about 4 carbon atoms; $R_3$ is one or more substituents selected from the group consisting of hydrogen, substituted and unsubstituted, saturated or unsaturated alkyl having from I to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof.

5. An orthodontic or peridontal method according to claim 2, wherein Z is pyridine.

6. An orthodontic or peridontal method according to claim 3 wherein Z is pyridine.

7. An orthodontic or peridontal method according to claim 4, wherein Z is pyridine.

8. An orthodontic or peridontal method according to claim 2, wherein m+n=1.

9. An orthodontic or peridontal method according to claim 2, wherein m+n=2.

10. An orthodontic or peridontal method according to claim 2, wherein component (a) is characterized as from about 0.002% to about 10.000% of a geminal diphosphonic acid compound, or a pharmaceutically-acceptable salt or ester thereof, having the structure:

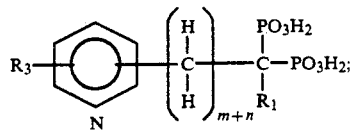

wherein m+n=1 or 2; $R_1$ is hydrogen, chloro, amino, or hydroxy; $R_3$ is one or more substituents selected from the group consisting of hydrogen, methyl, amino, chloro, methoxy, hydroxy, nitro, and combinations thereof; and the carrier (b) is a toothpaste, mouthwash, topical gel, or prophylaxis paste.

11. A orthodontic or peridontal method according to claim 10 wherein the diphosphonic acid compound is 3-pyridyl-1-hydroxy-ethylidene-1,1-bisphosphonic acid or a pharmaceutically acceptable salt or ester thereof.

* * * * *